US00PP29574P2

(12) United States Plant Patent
Yanny

(10) Patent No.: US PP29,574 P2
(45) Date of Patent: Aug. 7, 2018

(54) ***BUXUS* PLANT NAMED 'PROSTRATE 3'**

(50) Latin Name: ***Buxus* hybrid**
Varietal Denomination: Prostrate 3

(71) Applicant: JN Plant Selections, LLC, Milwaukee, WI (US)

(72) Inventor: Michael D. Yanny, Milwaukee, WI (US)

(73) Assignee: JN PLANT SELECTIONS, LLC, Milwaukee, WI (US)

( * ) Notice: Subject to any disclaimer, the term of this patent is extended or adjusted under 35 U.S.C. 154(b) by 0 days.

(21) Appl. No.: 15/731,193

(22) Filed: May 1, 2017

(51) Int. Cl.
*A01H 5/00* (2018.01)

(52) U.S. Cl.
USPC ..... Plt./226
CPC ..... *A01H 5/00* (2013.01)

(58) Field of Classification Search
USPC ..... Plt./226
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Buxus*, 'Prostrate 3', that is characterized by its low, spreading plant habit (much wider than its height), its plant size of 60 cm in width and 25 cm in height (lightly sheared) as a 7 year-old plant, and its cold hardiness at least to U.S.D.A Zone 5A.

2 Drawing Sheets

Botanical classification: *Buxus* hybrid.
Variety denomination: 'Prostrate 3'.

BACKGROUND OF THE INVENTION

The present invention relates to a new and distinct cultivar of *Buxus* of hybrid origin and will be referred to hereafter by its cultivar name, 'Prostrate 3'. 'Prostrate 3' is a new cultivar of boxwood grown for use as an ornamental landscape plant.

The new cultivar was developed from an ongoing breeding program conducted by the Inventor in Menomonee Falls, Wis. The objective of the breeding program was to select new cultivars of *Buxus* with improved hardiness in South East Wisconsin. 'Prostrate 3' arose as a seedling of open pollinated plants that were planted in 1990 with a mixture of seed collected of Sheridan hybrid plants (*Buxus sempervirens*×*Buxus microphylla* var. *koreana*). The exact parentage of the new cultivar is unknown. The likely seed parent of the new cultivar is believed to be *Buxus* 'Green Velvet' (not patented) based on the characteristics of the new cultivar and its presence in the seed mix. The Inventor selected the new cultivar as a single unique plant from amongst the seedlings of the above open pollinations in July of 2009.

Asexual propagation of the new cultivar was first accomplished by the Inventor by stem cuttings in July of 2009 in Menomonee Falls, Wis. Asexual propagation of the new cultivar by stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'Prostrate 3' as a unique cultivar of *Buxus*.

1. 'Prostrate 3' exhibits a low, spreading plant habit (much wider than its height).

2. 'Prostrate 3' exhibits a plant size of 60 cm in width and 25 cm in height (lightly sheared) as a 7 year-old plant.
3. 'Prostrate 3' exhibits cold hardiness at least to U.S.D.A Zone 5A.

The most likely seed parent of 'Prostrate 3', 'Green Velvet', differs from 'Prostrate 3' in being less compact and taller and wider at a younger age. 'Prostrate 3' can be most closely compared to *Buxus* cultivars 'Green Gem' (U.S. Plant Pat. No. 3,736) and 'Glencoe' (not patented). 'Green Gem' is similar to 'Prostrate 3' in having a compact plant habit and cold hardiness. 'Green Gem' differs from 'Prostrate 3' in having a taller and less wide plant habit. 'Glencoe' is similar to 'Prostrate 3' in cold hardiness. 'Glencoe' differs from 'Prostrate 3' in being less compact when mature and in having a taller and less wide plant habit.

BRIEF DESCRIPTION OF THE DRAWINGS

The accompanying colored photographs illustrate the overall appearance and distinct characteristics of the new *Buxus*. The photographs were taken of plants grown outdoors at a nursery in Menomonee Falls, Wis.

The photograph in FIG. 1 provides a side view of the low growing plant habit of 'Prostrate 3' taken of a plant 7 years in age.

Figure 1:
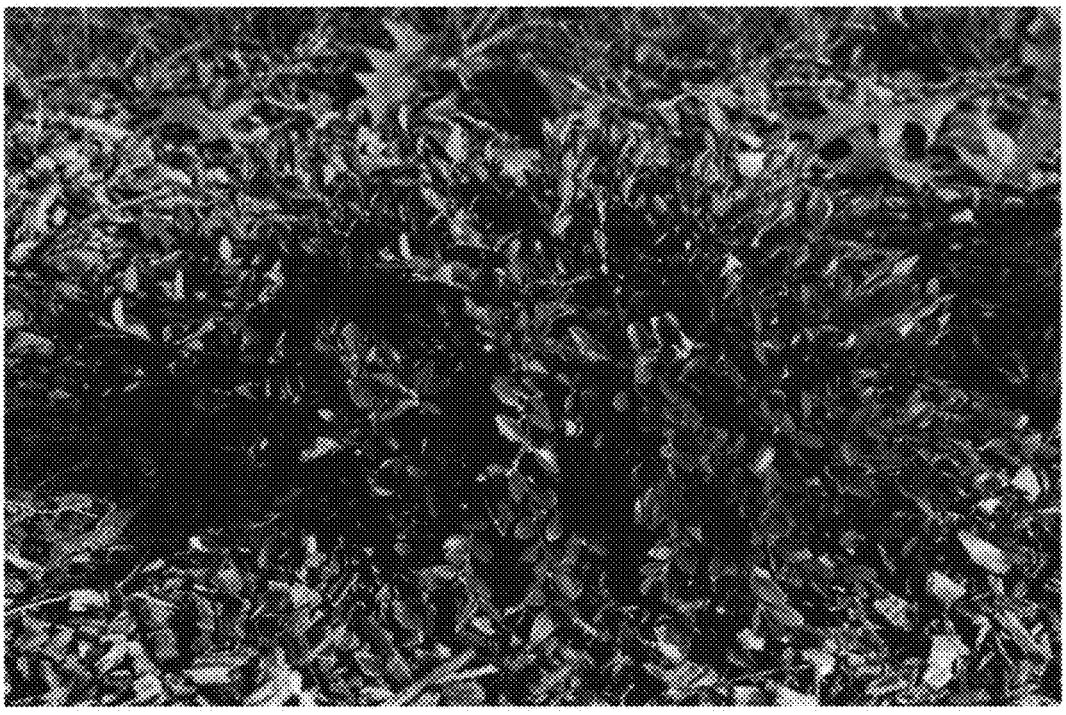
Figure 2:
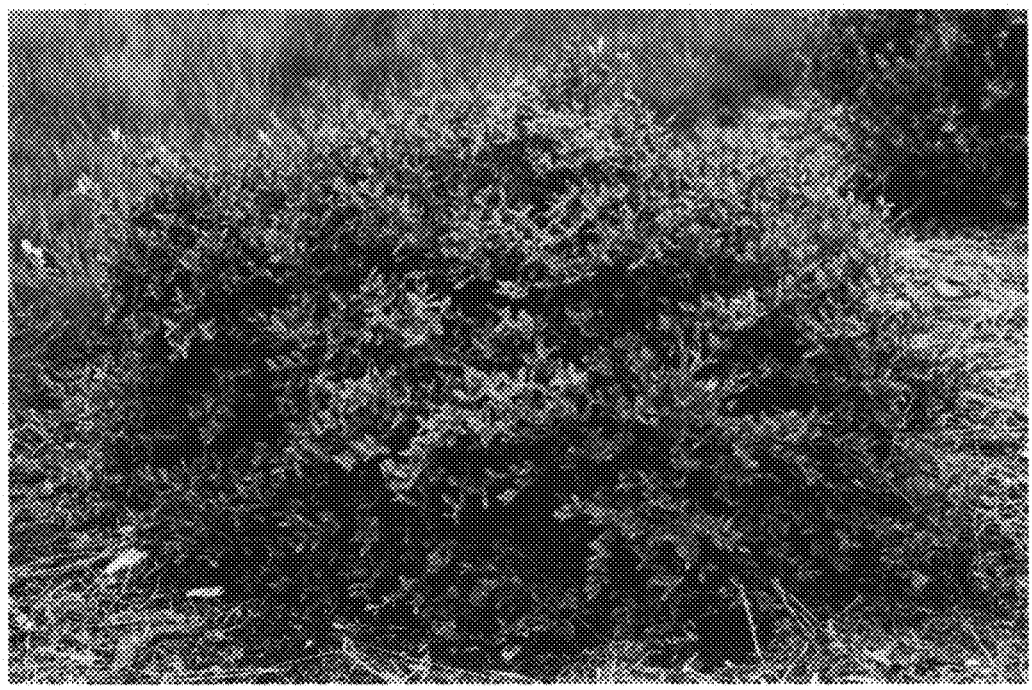

The photograph in FIG. 2 provides a side view of 'Prostrate 3' taken of a plant 25 years in age.

Figure 3:
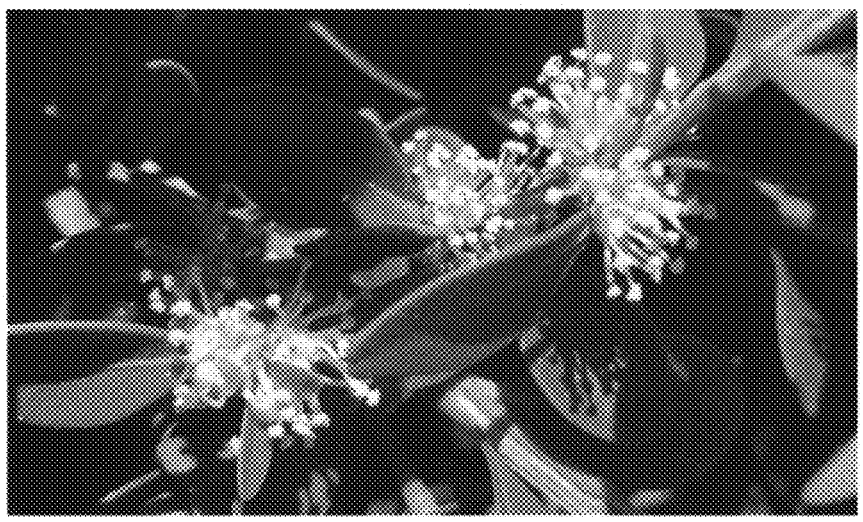

The photograph in FIG. 3 provides a close-up view of the inflorescences of 'Prostrate 3' taken of a plant 7 years in age.

The colors in the photographs are as close as possible with the photographic and printing technology utilized and the color values cited in the detailed botanical description accurately describe the colors of the new *Buxus*.

DETAILED BOTANICAL DESCRIPTION

The following is a description of 7 year-old plants as grown outdoors in five-gallon containers in Menomonee Falls, Wis. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type*.—Evergreen shrub.

*Plant habit*.—Compact, dense, low growing and spreading.

*Height and spread*.—Reaches an average of 60 cm in width and 25 cm in height as a 7 year-old plant in the landscape (lightly sheared).

*Cold hardiness*.—At least to U.S.D.A. Zone 5A with testing being conducted in Zones to 3B).

*Diseases resistance*.—No resistance or susceptibility to diseases has been observed.

*Root description*.—Fibrous, 161A in color.

*Propagation*.—Stem cuttings.

*Root development*.—Cuttings placed in mid July take 6 to 8 weeks to initiate rooting, 8 to 10 weeks to fully develop roots for planting in a container.

*Growth rate*.—Moderate.

Stem description:

*Shape*.—Round to slightly quadrangular.

*Stem color*.—Young stems; 144A, mature stems; a blend of 144A and 199A and 161D, trunk; a blend of 199A and 161D.

*Stem size*.—Main stems; average of 17 cm in length and 3 cm in diameter, lateral branches emerging from main stems; average of 16 cm in length and 3 mm in diameter, tertiary branches emerging from the lateral branches; average of 7 cm in length and 1 mm in diameter.

*Stem strength*.—Strong.

*Stem surface*.—Young stems; glabrous and smooth, mature stems; a blend of glabrous and rugose, trunk; rugose, dull, bark-like.

*Branch number*.—An average of 3 main stems, average number of branches per main stem; an average of 16 lateral branches emerging from main stems and an average of 10 tertiary branches emerging from the lateral branches.

*Branching habit*.—Stems arise from base, branches held in multiple angles.

Foliage description:

*Leaf shape*.—Lanceolate.

*Leaf division*.—Simple.

*Leaf base*.—Attenuate.

*Leaf apex*.—Varying between obtuse and retuse.

*Leaf fragrance*.—Light fresh fragrance.

*Leaf venation*.—Pinnate, midrib; upper surface 146B, lower surface 145B, with other veins matching leaf color.

*Leaf margins*.—Entire.

*Leaf arrangement*.—Opposite.

*Leaf attachment*.—Petiolate.

*Internode length*.—Average of 1 cm.

*Leaf surface*.—Glabrous and shiny on upper surface, glabrous and slightly less glossy, on lower surface.

*Leaf texture*.—Slightly thick, tough and waxy.

*Leaf size*.—Up to an average of 2 cm in length and 1 cm in width.

*Leaf quantity*.—Average of 110 on a branch 23 cm in length.

*Leaf color*.—Young and mature leaves; upper surface 139A, young and mature lower surface; 146B with thin margins 139A.

*Petioles*.—Average of 5 mm in length and 1 mm in width, both sides are 146B in color and glabrous.

Inflorescence description (primarily staminate with some perfect flowers):

*Significance*.—Flowers are insignificant and non-showy.

*Blooming period*.—2 to 3 weeks in very early spring in S. E. Wisconsin, commencing in early to mid April.

*Inflorescence*.—Arranged in alternate pairs of single flowers at upper leaf axils.

*Inflorescence size*.—Average of 1.5 cm in width, 7 mm in height.

*Lastingness of inflorescence*.—Average of one week.

*Inflorescence fragrance*.—Pleasant fragrance, medium strength when in full bloom.

*Flower buds*.—Clusters are round in shape, size of cluster is 4 mm in diameter and length, individual buds are round to flat in shape, size of individual bud is 2 mm in diameter and length, surface is matte and dry, color is a blend of N155B and 157A with a light flush of 182C.

*Flower type*.—Primarily androecious and comprised of tight rounded clusters of male stamens with some flowers, perfect.

*Male and female flowers*.—Average of 1.5 cm in height and 3 mm in width, apetalous, sepals; 4, about 5 mm in diameter, glabrous surface, sessile to node, cuneate base and apex, 145B to 145C in color.

Reproductive organs:

*Stamens*.—50, conspicuous and emerge from a pistillode (about 1 cm in diameter and 145C in color), filament; 3 mm in length and 145D in color, anthers; up to 2 mm in diameter, between 146A and 145D in color, pollen is moderate and 8D in color.

*Pistils*.—1, 3-parted, styles; 3, N144C in color, 1 mm in length, stigma; 2-parted, decurrent, 145C in color, 1 mm in length, ovary; 145B in color and 2 mm in length, 3 mm in width.

*Fruit and seed*.—None observed to date.

It is claimed:

1. A new and distinct cultivar of *Buxus* plant named 'Prostrate 3' as herein illustrated and described.

* * * * *